US008822917B2

(12) United States Patent
Ueda et al.

(10) Patent No.: US 8,822,917 B2
(45) Date of Patent: Sep. 2, 2014

(54) METHOD FOR ANALYZING GLYCAN STRUCTURE

(71) Applicants: Riken, Wako (JP); Shimadzu Corporation, Kyoto (JP)

(72) Inventors: Koji Ueda, Wako (JP); Atsuhiko Toyama, Kyoto (JP)

(73) Assignees: Riken, Saitama (JP); Shimadzu Corporation, Kyoto (JP)

( * ) Notice: Subject to any disclaimer, the term of this patent is extended or adjusted under 35 U.S.C. 154(b) by 0 days.

(21) Appl. No.: 14/147,928

(22) Filed: Jan. 6, 2014

(65) Prior Publication Data

US 2014/0117225 A1 May 1, 2014

Related U.S. Application Data

(63) Continuation of application No. 13/943,130, filed on Jul. 16, 2013, now Pat. No. 8,653,448.

(30) Foreign Application Priority Data

Sep. 7, 2012 (JP) ................................. 2012-197908

(51) Int. Cl.
*B01D 59/44* (2006.01)
*H01J 49/00* (2006.01)

(52) U.S. Cl.
CPC ............. *H01J 49/0027* (2013.01); *B01D 59/44* (2013.01); *H01J 49/00* (2013.01)
USPC ........... 250/282; 250/281; 250/283; 250/297; 250/288; 250/289; 250/290; 250/291; 250/292; 436/110; 436/173; 506/6; 506/19

(58) Field of Classification Search
USPC ................................... 250/281–283, 287–292
See application file for complete search history.

(56) References Cited

U.S. PATENT DOCUMENTS

| 8,653,448 | B1 * | 2/2014 | Ueda et al. ..................... 250/282 |
| 2008/0139396 | A1 * | 6/2008 | Kameyama et al. .............. 506/6 |
| 2008/0254996 | A1 * | 10/2008 | Kanie et al. ....................... 506/6 |

FOREIGN PATENT DOCUMENTS

| JP | 2005-265697 A | 9/2005 |
| JP | 2006-145519 A | 6/2006 |
| JP | 2008-309501 A | 12/2008 |
| JP | 2012-58002 A | 3/2012 |
| WO | WO-2006/043405 A1 | 4/2006 |

OTHER PUBLICATIONS

Flynn, Gregory C. et al., "Naturally occurring glycan forms of human immunoglobulins G1 and G2", Molecular Immunology, 2010, vol. 47, pp. 2074-2082.

(Continued)

*Primary Examiner* — Jack Berman
*Assistant Examiner* — Meenakshi Sahu
(74) *Attorney, Agent, or Firm* — Cheng Law Group, PLLC

(57) ABSTRACT

In order to provide an analysis method that is capable of determining a glycan structure with high detection sensitivity, a method of the present invention includes the steps of: carrying out triple quadrupole mass spectrometry at various values of CID energy; creating an energy-resolved profile including yield curves representing relationships between (i) a value of the CID energy and (ii) measured amounts of specific types of product ions; preparing a reference profile, and identifying a glycan structure of a test material by comparing the energy-resolved profile with the reference profile.

8 Claims, 8 Drawing Sheets

(56) References Cited

OTHER PUBLICATIONS

Shinkawa, Toyohide et al., "Glycobiology and Extracellular Matrices: The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, 2003, vol. 278, pp. 3466-3473.

Kurogochi, Masaki et al., "Sialic Acid-focused Quantitative Mouse Serum Glycoproteomics by Multiple Reaction Monitoring Assay", Molecular & Cellular Proteomics, 2010, vol. 9, No. 11, pp. 2354-2368.

Ueda, Koji at al., "Evaluating the biosimilars: Energy Resolved Oxonium Ion Monitoring (Erexim) technology for the analysis of N-glycan microheterogeneity in therapeutic antibodies", Abstract for HUPO 11th Annual World Congress, Sep. 2012, http://hupoabstracts.inmerge.com/Default.aspx?tabid=80&type=search.

* cited by examiner

METHOD FOR ANALYZING GLYCAN STRUCTURE

CROSS-REFERENCE TO RELATED APPLICATIONS

This application is a Continuation application of patent application Ser. No. 13/943,130, filed on Jul. 16, 2013, which is based on Japanese Application No. 2012-197908, filed on Sep. 7, 2012, the entire contents of which are hereby incorporated by reference.

TECHNICAL FIELD

The present invention relates to a method for analyzing a glycan structure. More specifically, the present invention relates to a method for analyzing a glycan structure by triple quadrupole mass spectrometry.

BACKGROUND ART

Foreseeing the patent expiry of therapeutic antibodies that are selling more than $30 billion worldwide, there is growing interest over how biosimilar substitutes could win FDA-approval in the near future. The first draft guidance on the evaluation of biosimilarity was published by FDA in February 2012, in which emphasis was placed on the importance of evaluating minor structural differences that can significantly affect the potency and safety of biopharmaceuticals, with specific reference to glycosylation patterns, and that such structural characterization be conducted on multiple lots to understand the lot-to-lot variability.

With regard to therapeutic antibodies, which have a common N-glycosylation consensus sequence at $Asn_{297}$ in the conserved (Fc) region of heavy chain, some specific features of N-glycosylation have been characterized to affect potency and safety. For example, absence of core fucosylation was demonstrated to enhance antibody-dependent cellular cytotoxicity by 10-fold. Moreover, recent studies revealed that non-human oligosaccharide motifs such as glycolylneuraminic acid (Neu5Gc) and galactose-α1,3-galactose (α-Gal epitope) are immunogenic and can cause anaphylaxis in patients expressing specific IgE. Further characterization elucidated more specifically that immunogenicity of α-Gal epitope was primarily attributed to an extra N-glycan occurring within the antigen-binding (Fab) region. These findings have raised the issue of antibody glycosylation to the level that global picture of its heterogeneity and biological impact is urgently needed.

Here, glycans of glycoproteins are explained. The glycans of glycoproteins are largely classified into two types of glycans, i.e., (i) N-glycoside-linked glycans (N-glycans) linked to an asparagine residue and (ii) O-glycoside-linked glycans (O-glycans) linked to serine, threonine, or the like. The N-glycans have a common core structure (see the following structural formula) whose terminal linked to asparagine is referred to as a reducing terminal and whose terminal opposite to the reducing terminal is referred to as a nonreducing terminal.

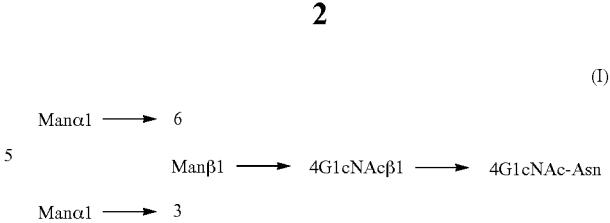

(I)

The N-glycans are classified into (i) high-mannose type having more than one mannose linked to the nonreducing terminal of the core structure, (ii) complex type having, at the nonreducing terminal, one or more N-acetylglucosamine (hereinafter referred to as GlcNAc) branches to each of which galactose, sialic acid, fucose, and the like are linked, and (iii) hybrid type having both a high-mannose type branch and a complex type branch. It is well known that, for example, the complex type and the hybrid type can have GlcNAc linked to mannose at a branching point of the core structure (bisecting GlcNAc) and can have fucose linked to GlcNAc at the reducing terminal (core fucose).

Such a structural diversity is observed in a single glycoprotein, and is called, for example, Glycoform Heterogeneity. For example, one paper reports that a glycan structure analysis of human serum immunoglobulin G having a single N-glycan binding site revealed that the human serum immunoglobulin G had 34 types of glycan structures (Non Patent Literature 1).

As described above, recent studies revealed that differences in glycan structure significantly affect functions of glycoproteins (see, for example, Non Patent Literature 2). Accordingly, there are demands for a method for a quantitative analysis of glycan structures having diversity and highly efficient profiling as to types and proportions of the glycan structures.

One example of the method for analyzing a glycan structure is a method of (i) chemically or enzymatically isolating an N-glycan from a glycoprotein, (ii) chemically modifying (labeling) and purifying the N-glycan, and then (iii) detecting the N-glycan by a combination of HPLC and mass spectrometry such as MALDI-TOF MS. This method has advantages such as (i) being capable of easily separating labeled glycans according to structure by reversed-phase or normal-phase HPLC and (ii) being capable of removing impurities through the purification and thereby allowing highly sensitive measurement. On the other hand, this method has disadvantages such as (i) requiring complicated pretreatment and (ii) being incapable of obtaining information of each glycosylation site in a case where the glycoprotein has more than one glycosylation sites.

Another example is a method of (i) breaking a glycoprotein into glycopeptides, which are peptides to which a glycan is linked, by an enzyme such as trypsin and then (ii) measuring the glycopeptides thus obtained (Patent Literature 1). This measurement is carried out mostly by use of a mass spectrometer using nano HPLC-ESI as an ion source. This mass spectrometer makes it possible to not only accumulate glycopeptide-derived signals and quantify glycopeptide but also determine a glycosylation site and estimate a glycan structure through $MS^n$ measurement. Another paper reports a method of measuring a fragment ion specific to each glycopeptide with good quantitativity with the use of a triple quadrupole mass spectrometer by a multiple reaction monitoring (MRM) method (Non Patent Literature 3).

CITATION LIST

Patent Literature 1

Japanese Patent Application Publication, Tokukai, No. 2008-309501 A (Publication Date: Dec. 25, 2008)

Patent Literature 2

Japanese Patent Application Publication, Tokukai, No. 2012-58002 A (Publication Date: Mar. 22, 2012)

Patent Literature 3

Japanese Patent Application Publication, Tokukai, No. 2005-265697 A (Publication Date: Sep. 29, 2005)

Patent Literature 4

Japanese Patent Application Publication, Tokukai, No. 2006-145519 A (Publication Date: Jun. 8, 2006)

Patent Literature 5

WO2006/043405 (Publication Date: Apr. 27, 2006)

Non Patent Literature 1

Flynn, G. C. et al., Naturally occurring glycan forms of human immunoglobulins G1 and G2., Mol Immunol, 2010, 47, 2074-2082.

Non Patent Literature 2

Shinkawa, T. et al., The absence of fucose but not the presence of galactose or bisecting N-acetylglucosamine of human IgG1 complex-type oligosaccharides shows the critical role of enhancing antibody-dependent cellular cytotoxicity., J Biol Chem, 2003, 278, 3466-3473.

Non Patent Literature 3

Kurogochi, M. et al., Sialic acid-focused quantitative mouseserum glycoproteomics by multiple reaction monitoring assay., Mol Cell Proteomics, 2010, 9, 2354-2368.

SUMMARY OF INVENTION

Technical Problem

The conventional methods, however, have problems such as (i) low sensitivity of detection of glycopeptides in a mixture of peptides with no glycan and the glycopeptides and (ii) difficulty of detecting a glycan structure even by MS/MS analysis of glycopeptides. In addition, since the detection sensitivity of glycopeptides is low, it is not easy to determine a glycan structure.

The present invention was accomplished in view of the above problems, and an object of the present invention is to provide a method for analyzing a glycan structure with high detection sensitivity.

Solution to Problem

A method of the present invention for analyzing a glycan structure of a test material having a glycan, includes the steps of: (a) measuring specific types of product ions produced from the test material at various values of CID energy by MS/MS; (b) creating an energy-resolved profile including yield curves representing relationships between (i) the values of the CID energy and (ii) measured amounts of the respective specific types of product ions; (c) preparing a reference profile including yield curves representing relationships between (i) the values of the CID energy and (ii) measured amounts of respective same types of product ions produced from a reference test material as the specific types of product ions, the reference test material being a test material having a glycan and whose structure is known; and (d) identifying the glycan structure of the test material by comparing the energy-resolved profile obtained in the step (b) with the reference profile, the specific types of product ions including at least two types of product ions derived from a protonated monosaccharide or disaccharide, and in the step (a), the measurement by MS/MS being carried out by use of a mass spectrometer which causes no Low-mass cutoff.

Advantageous Effects of Invention

According to the present invention, it is possible to determine a glycan structure of a test material with high detection sensitivity.

DESCRIPTION OF EMBODIMENTS

Figure 1:
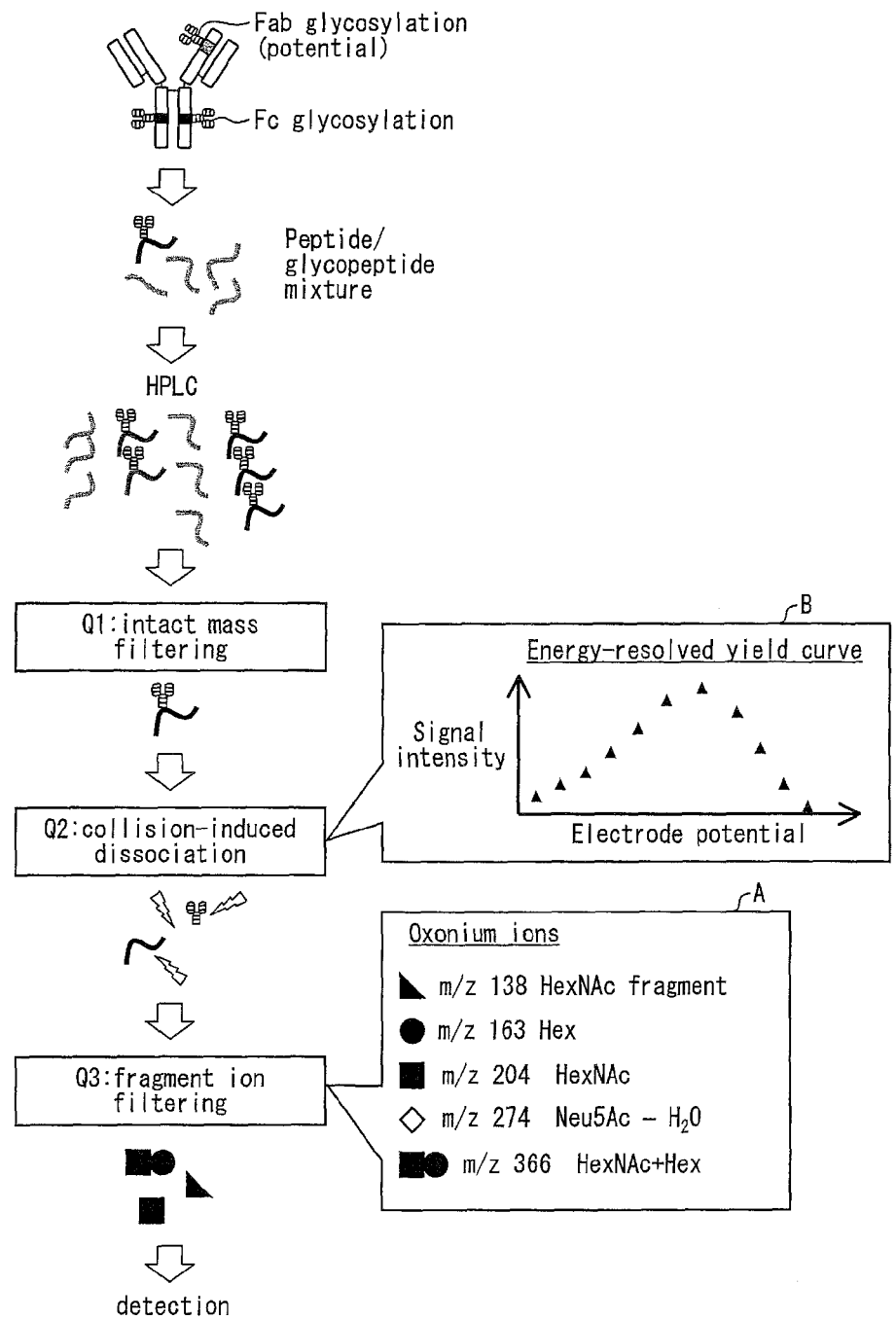
FIG. 1 is a view schematically showing a scheme by which an energy-resolved yield curve of oxonium ions can be acquired by using a triple quadrupole mass spectrometer.

An embodiment of a method of the present invention for analyzing a glycan structure is described below.

A method of the present embodiment for analyzing a glycan structure of a test material having a glycan includes: the step (measuring step) of measuring specific types of product ions produced from the test material at various values of CID energy by MS/MS; the step (creating step) of creating an energy-resolved profile including yield curves representing relationships between (i) the values of the CID energy and (ii) measured amounts of the respective specific types of product ions; the step (preparing step) of preparing a reference profile including yield curves representing relationships between (i) the values of the CID energy and (ii) measured amounts of respective same types of product ions produced from a reference test material as the specific types of product ions, the reference test material being a test material having a glycan and whose structure is known; and the step (identifying step) of identifying the glycan structure of the test material by comparing the energy-resolved profile obtained in the creating step with the reference profile, the specific types of product ions including at least two types of product ions derived from a protonated monosaccharide or disaccharide, and in the measuring step, the measurement by MS/MS being carried out by use of a mass spectrometer which causes no Low-mass cutoff.

The inventors of the present invention found that a pattern of an energy-resolved profile obtained in a similar step to the measuring step and the creating step is determined by a glycan structure and differs from one glycan structure to another. Based on this finding, the inventors of the present invention accomplished the present analysis method.

The following description deals with an example in which a triple quadrupole mass spectrometer, which causes no Low-mass cutoff, is used as a mass spectrometer for measurement. Note, however, that the mass spectrometer to be used is not limited to this.

(1. Measuring Step)

The measuring step is a step of measuring specific types of product ions at various values of CID energy by triple quadrupole mass spectrometry.

The term "CID energy" used herein refers to energy which is applied when ions (precursor ions) corresponding to a test material to be measured are subjected to CID (collision induced dissociation) at a second quadrupole of the triple quadrupole mass spectrometer. Parameters for regulating the CID energy can vary depending on which device is used. In general, the "CID energy" refers to a voltage for oscillating ions in a cell in which the CID is carried out. The term "product ions" used herein refers to fragment ions generated as a result of the CID on the precursor ions. The "m/z" used herein refers to a mass (m) to charge (z) ratio.

It is possible to measure the product ions at various values of the CID energy by appropriately setting the CID energy in a range suitable for a used device, but the CID energy is preferably changed as follows:

(i) The CID energy is changed from energy at which a relative intensity of the precursor ions is 100 (i.e., only the precursor ions are detected) to energy at which the relative intensity of the precursor ions is 0.

(ii) The CID energy is changed within a range including an energy point which provides the maximum intensity of each type of product ions.

(iii) The CID energy is changed, for each type of product ions, within a range which includes an energy point which provides the maximum intensity of the each type of product ions and which ranges from minimum energy for detection of the each type of product ions to energy at which the intensity of the each type of product ions is 0.

In the present embodiment, the specific types of product ions to be measured are, out of product ions of the test material, product ions derived from a protonated monosaccharide or disaccharide, and are, for example, product ions having m/z in a range from 100 to 500. Specific examples of such product ions encompass product ions having m/z of 163, 168, 186, 204, 274, 290, 292, 308, 366, 454, and 470, respectively. The product ion having m/z of 163 corresponds to an oxonium ion of hexose (Hex). The product ion having m/z of 168 corresponds to an oxonium ion of N-acetylhexosamine-2H$_2$O (HexNAc-2H$_2$O). The product ion having m/z of 186 corresponds to an oxonium ion of N-acetylhexosamine-H$_2$O (HexNAc—H$_2$O). The product ion having m/z of 204 corresponds to an oxonium ion of N-acetylhexosamine (HexNAc). The product ion having m/z of 274 corresponds to an oxonium ion of 5-acetylneuraminic acid-H$_2$O (Neu5Ac—H$_2$O). The product ion having m/z of 290 corresponds to an oxonium ion of 5-glycolylneuraminic acid-H$_2$O (Neu5Gc-H$_2$O). The product ion having m/z of 292 corresponds to an oxonium ion of 5-acetylneuraminic acid (Neu5Ac). The product ion having m/z of 308 corresponds to an oxonium ion of 5-glycolylneuraminic acid (Neu5Gc). The product ion having m/z of 366 corresponds to an oxonium ion of N-acetylhexosamine+hexose (HexNAc+Hex). The product ion having m/z of 454 corresponds to an oxonium ion of 5-acetylneuraminic acid+hexose (Neu5Ac+Hex). The product ion having m/z of 470 corresponds to an oxonium ion of 5-glycolylneuraminic acid+hexose (Neu5Gc+Hex).

Note, however, that the product ions to be measured are not limited to those mentioned above. For example, the product ions to be measured may include a product ion having m/z of 138 and/or a product ion having m/z of greater than 500.

In a case of using an expression "the specific types of product ions include product ions having m/z of 163, 204, 274, and 366, respectively", the expression means that (i) at least these four types of product ions having m/z of 163, 204, 274, and 366, respectively, are measured and (ii) another/other type(s) of product ions having another/other value(s) of m/z may be additionally measured. For example, a product ion having m/z of 138 may be measured in addition to these four types of product ions. That is to say, the measuring step may be (i) a step of measuring only the product ions having m/z of 163, 204, 274, and 366, respectively, (ii) a step of measuring only the product ions having m/z of 138, 163, 204, 274, and 366, respectively, or (iii) a step of measuring another/other type(s) of product ions in addition to these types of product ions. Note that the product ion having m/z of 138 corresponds to an oxonium ion of a fragment of HexNAc.

In the present analysis method, an energy-resolved profile including a plurality of yield curves is created. Accordingly, the product ions to be measured include at least two types of product ions, preferably include at least two types of product ions selected from the group consisting of product ions having m/z of 163, 168, 186, 204, 274, 290, 292, 308, 366, 454, and 470, respectively, more preferably include (i) at least one type of product ion selected from the group consisting of product ions having m/z of 163, 168, 186, 274, 290, 292, 308, 366, 454, and 470, respectively and (ii) the product ion having m/z of 204, further more preferably include product ions having m/z of 163, 204, 274, and 366, respectively.

As described above, the product ions are measured at various values of the CID energy. Note, however, that an amount by which the value of the CID energy is changed is not limited in particular. For example, the value of the CID energy can be changed at increments of 3V to 5V.

Use of the triple quadrupole mass spectrometer makes it possible to avoid the following problems arising from Low-mass cutoff. For example, in a case where a mass spectrometer, such as a quadrupole ion trap mass spectrometer, which causes Low-mass cutoff is used, sensitivity of detection of fragment ions in a low mass range (e.g., m/z=100 to 300) in MS/MS measurement depends on m/z of precursor ions. This means that in a case where, for example, the test material to be measured is a glycopeptide which contains peptides in addition to glycans, m/z of the precursor ions becomes large, which leads to a problem such as a failure to detect the fragment ions in the low mass range or low sensitivity of detection of the fragment ions in the low mass range. Furthermore, in such a case where the test material to be measured is a glycopeptide, the following problem occurs. Even glycopeptides having an identical glycan structure can vary in total mass from one another if they are different from one another in amino acid sequence of a peptide. A difference in m/z of precursor ions results in, due to Low-mass cutoff, a difference in sensitivity of detection of fragment ions in the low mass range. It is therefore expected that glycopeptides which have an identical glycan structure but are different from each other in amino acid sequence are different from each other in obtained yield curve and energy-resolved profile (later described). It is therefore preferable to carry out MS/MS measurement with the use of a triple quadrupole mass spectrometer, which causes no Low-mass cutoff. Note, however, that a mass spectrometer to be used is not limited to a triple quadrupole mass spectrometer, provided that it causes no Low-mass cutoff and is capable of successively acquiring MS/MS measurement data on an identical precursor ion at various values of the CID energy. The mass spectrometer which causes no Low-mass cutoff can be any mass spectrometer whose sensitivity of detection of fragment ions in a low mass range (e.g., m/z=100 to 300) does not depend on m/z of precursor ions.

Examples of a method for ionization encompass FAB (fast atom bombardment), CI (chemical ionization), ESI (electrospray ionization), MALDI (matrix-assisted laser desorption/ionization), and APCI (atmospheric pressure chemical ionization). Above all, ESI is suitably used. Examples of ESI encompass microspray ionization and nanospray ionization. Of the two examples of ESI, the nanospray ionization is suitably used.

The test material to be analyzed in the present analysis method is not limited in particular, provided that it is a test material which has a glycan and can be subjected to triple quadrupole mass spectrometry. Suitably, the test material to be analyzed is a glycoprotein or a glycopeptide. The glycoprotein and the glycopeptide each may be one obtained from a biological tissue, a biological cell, or the like or may be one obtained by adding a glycan to an artificially synthesized protein or peptide. The glycopeptide may be one obtained through acid hydrolysis or enzymatic decomposition of a glycoprotein. In a case where the glycopeptide is obtained through decomposition of a glycoprotein, the number of glycosylation sites of the glycoprotein is not limited to 1, but the glycoprotein may have more than 1 glycosylation site. Further, in the case where the glycopeptide is obtained through decomposition of a glycoprotein, it is preferable to use a glycopeptide that has been subjected to separation and purification by HPLC or the like. The glycoprotein and the glycopeptide each may have an N-glycan or may have an O-glycan. N-glycans, which have the common core structure, are expected to have the smaller number of variations of the energy-resolved profile (later described) than O-glycans. It is therefore easier to identify a glycan structure of an N-glycan than a glycan structure of an O-glycan. The present method is therefore more suitably applied to a glycoprotein having an N-glycan or a glycopeptide having an N-glycan.

(2. Creating Step)

The creating step is a step of creating an energy-resolved profile (referred to also as an energy-resolved oxonium ion profile) which includes yield curves representing relationships between (i) the CID energy and (ii) measured amounts of the respective specific types of product ions.

Each of the yield curves (referred to also as energy-resolved yield curves) representing relationships between the CID energy and measured amounts of respective types of product ions can be created, for example, by plotting measured amounts (counted values) (represented by a y-axis) of a target product ion against values of the CID energy (represented by an x-axis). The measured amounts of the target product ion which are to be plotted may be relative amounts to another type of product ion or may be a ratio to the total counted values of all the measured product ions. In one aspect of the present embodiment, yield curves are created in such a manner that (i) a product ion having m/z of 138 is measured and (ii) a measured amount of the target product ion is normalized with the use of a measured amount of this product ion. More specifically, in the measuring step, the product ion having m/z of 138 is measured in addition to the other specific types of product ions. A value of the CID energy at which a measured amount of this product ion becomes maximum is determined. Then, the measured amount of this product ion at the value thus determined is assumed to be a standard value 100. Measured amounts of the other specific types of product ions are expressed as relative values to the standard value. The measured amounts of the other specific types of product ions are thus normalized.

The energy-resolved profile is a profile, for a single test material, which combines (unifies) yield curves of the respective specific types of product ions. That is, in a case where four specific types of product ions are measured, the energy-resolved profile includes four yield curves.

(3. Preparing Step)

The preparing step is a step of preparing a reference profile which includes yield curves representing relationships between (i) a value of the CID energy and (ii) measured amounts of respective same types of product ions produced from a reference test material as the specific types of product ions measured in the measuring step, which reference test material is a test material which has a glycan and whose structure is known.

The expression "preparing a reference profile" used herein encompasses not only a case where a reference profile is newly created, but also a case where a reference profile that has been already created is made available. The expression "made available" means, for example, obtaining a reference profile that has been already created or allowing an access to a server or the like in which the reference profile is stored. The "reference profile that has been already created" may be one created by another person. The "same types of product ions" refer to types of product ions having same values of m/z as the specific types of product ions measured in the measuring step.

The reference profile is same in nature as the energy-resolved profile, and is obtained from a reference test material whose structure including a glycan portion is known. The term "structure" used herein refers to, in the case of a glycan, a sequence of the glycan and positions at which sugars are linked, and refers to, in the case of a protein or a peptide, an amino acid sequence thereof and positions at which glycans are linked.

The reference test material is a test material of the same type as the test material to be analyzed in the present analysis method. That is, in a case where the test material to be analyzed is a glycopeptide, the reference test material is a glycopeptide as well. Further, in a case where the test material to be analyzed is a glycopeptide having an N-glycan, the reference test material is a glycopeptide having an N-glycan as well. Note, however, that even in such cases where the test material to be analyzed and the reference test material are glycopeptides, the test material to be analyzed and the reference test material need not be same in amino acid sequence of a peptide.

The reference profile can be created according to the methods used in the measuring step and the creating step. Specifically, triple quadrupole mass spectrometry is carried out while changing a value of the CID energy so that, out of types of product ions produced from the reference test material, the same types of product ions as the types of the specific types of product ions are measured at various values of the CID energy. Then, yield curves are created which represent relationships between (i) the value of the CID energy and (ii) measured amounts of the respective types of the product ions thus measured. Then, a reference profile combining these yield curves is created. It is only necessary that the types of product ions measured for creation of the reference profile include the same types of product ions as the specific types of product ions. That is, another/other type(s) of product ions having another/other value(s) of m/z may be additionally measured. In a case where the yield curves included in the energy-resolved profile of the test material to be analyzed are normalized, the yield curves included in the reference profile are normalized as well.

The reference profile thus obtained is associated with the test material which was used for creation of the reference profile and whose structure is known. That is, a reference profile is associated with a glycan structure of a test material used for creation of the reference profile. One reference profile can be distinguished from another according to a difference in pattern of yield curves included therein. That is, differences in glycan structure among test materials result in creation of reference profiles of different patterns.

In the identifying step (described later), the energy-resolved profile of the test material to be analyzed is compared with reference profiles thus prepared, and in a case where a reference profile that is identical to the energy-resolved profile is found, the glycan structure of the test material to be analyzed is identified as a glycan structure associated with the reference profile thus found. That is, whether a glycan structure can be identified or not in the identifying step depends on whether a reference profile associated with the glycan structure is prepared or not. It is therefore preferable to prepare reference profiles for a larger number of glycan structures.

(4. Identifying Step)

The identifying step is a step of identifying a glycan structure of the test material to be analyzed by comparing the energy-resolved profile obtained in the creating step with the reference profile.

Specifically, the energy-resolved profile of the test material to be analyzed which energy-resolved profile is obtained in the creating step is compared with prepared reference profiles. In a case where a reference profile that is identical to the energy-resolved profile is found, the glycan structure of the test material to be analyzed is identified as a glycan structure associated with the reference profile thus found. In a case where no reference profile that is identical to the energy-resolved profile is found, the glycan structure of the test material to be analyzed is identified as any of glycan structures other than the glycan structures associated with the prepared reference profiles.

A method for determining whether the energy-resolved profile is identical to a reference profile or not is not limited to a specific one, and can be a known pattern recognition technique. Examples of the known pattern recognition technique encompass a prediction approach using linear regression analysis.

(5. Quantifying Step)

In addition to the above steps, the method of the present embodiment for analyzing a glycan structure further includes the step (quantifying step) of quantifying the test material with the use of a standard material whose concentration is known.

The quantifying step is a step of quantifying the test material to be analyzed by comparing (i) a measured amount of a product ion having m/z of 138 produced from the test material to be analyzed and (ii) a measured amount of a product ion having m/z of 138 produced from the standard material whose concentration is known. It is preferable that the product ion having m/z of 138 be measured at CID energy at which generation efficiency of this product ion becomes maximum. The expression "generation efficiency becomes maximum" used herein also encompasses a case where generation efficiency is estimated to become maximum. The concentration of the standard material can be measured in advance by a known quantification technique such as UV absorbance measurement. In a case where the test material to be analyzed is a glycopeptide, the standard material is preferably a glycopeptide as well, more preferably a glycopeptide having an identical amino acid sequence to that of the glycopeptide of the test material to be analyzed.

As demonstrated in Examples that will be described later, there is an extremely strong linear correlation between (i) a value of the CID energy at which generation efficiency of the product ion of m/z=138 becomes maximum and (ii) m/z of glycopeptides. It is therefore possible to obtain a value of the CID energy at which generation efficiency of the product ion of m/z=138 produced from the test material to be analyzed becomes maximum by multiplying m/z of the test material to be analyzed by a coefficient x/y where x is a value of the CID energy at which generation efficiency of the product ion of m/z=138 produced from the reference test material whose m/z is known becomes maximum and y is m/z of the reference test material. The value of the CID energy at which generation efficiency of the product ion of m/z=138 produced from the reference test material whose m/z is known becomes maximum can be easily obtained by measuring the product ion of m/z=138 produced from the reference test material at various values of the CID energy. In a case where the reference test material has an identical structure to that of the test material to be analyzed, it is possible to carry out the quantification more accurately.

Alternatively, the value of the CID energy at which generation efficiency of the product ion of m/z=138 produced from the test material to be analyzed becomes maximum can be obtained based on (i) m/z of the test material to be analyzed and (ii) a calibration curve which is created by carrying out linear regression analysis with the use of values of the CID energy, for respective plural reference test materials whose m/z is known, at which generation efficiency of the product ion of m/z=138 becomes maximum.

As described above and as demonstrated in Examples that will be described later, the method of the present invention for analyzing a glycan structure is an extremely versatile method which is capable of selectively measuring a target substance, in a test material, having a glycan with high sensitivity. Accordingly, the method of the present invention for analyzing a glycan structure is applicable to experiments and researches in general targeted at a glycan. In industrial fields, there are high demands for a quality control test for glycan structures of biotechnology-based drugs which have formed a huge market. Therefore, wide ranging applications of the present invention are expected also in the industrial fields.

(Summary)

As described above, a method of the present invention for analyzing a glycan structure of a test material having a glycan, includes the steps of: (a) measuring specific types of product ions produced from the test material at various values of CID energy by MS/MS; (b) creating an energy-resolved profile including yield curves representing relationships between (i) the values of the CID energy and (ii) measured amounts of the respective specific types of product ions; (c) preparing a reference profile including yield curves representing relationships between (i) the values of the CID energy and (ii) measured amounts of respective same types of product ions produced from a reference test material as the specific types of product ions, the reference test material being a test material having a glycan and whose structure is known; and (d) identifying the glycan structure of the test material by comparing the energy-resolved profile obtained in the step (b) with the reference profile, the specific types of product ions including at least two types of product ions derived from a protonated monosaccharide or disaccharide, and in the step (a), the measurement by MS/MS being carried out by use of a mass spectrometer which causes no Low-mass cutoff.

According to the arrangement, an energy-resolved profile for a test material to be measured is created. The energy-resolved profile represents relationships between (i) CID energy in MS/MS measurement and (ii) measured amounts of respective specific types of product ions. The energy-resolved profile thus obtained is compared with a reference profile that is separately prepared. The reference profile is obtained from a test material whose structure is known. Accordingly, in the reference profile, an energy-resolved profile representing relationships between (i) CID energy in MS/MS measurement and (ii) measured amounts of respective specific types of product ions is associated with a glycan structure. It is therefore possible to identify the test material to be analyzed by comparing the energy-resolved profile for the test material to be analyzed and the reference profile. The product ions to be measured are product ions derived from a protonated monosaccharide or disaccharide, i.e., oxonium ions derived from a glycan. Therefore, measurement can be carried out irrespective of a structure other than a glycan part to be analyzed. Note that most of the product ions derived from a protonated monosaccharide or disaccharide are in a low mass range from 100 m/z to 500 m/z. According to the present analysis method, the MS/MS measurement is carried out by use of a mass spectrometer which causes no Low-mass cutoff. This makes it possible to measure product ions with high detection sensitivity without the need for a process for separating a glycan from the test material to be analyzed. Since a glycan is not separated in advance, it is possible to, even in a case where there are a plurality of precursor ions having respective glycan structures, distinguish product ions derived from the respective precursor ions.

The method of the present invention for analyzing a glycan structure is preferably arranged such that the specific types of product ions include at least two types of product ions selected from the group consisting of product ions having m/z of 163, 168, 186, 204, 274, 290, 292, 308, 366, 454, and 470, respectively. The method of the present invention for analyzing a glycan structure is more preferably arranged such that the specific types of product ions include (i) at least one type of product ion selected from the group consisting of product ions having m/z of 163, 168, 186, 274, 290, 292, 308, 366, 454, and 470, respectively and (ii) a product ion having m/z of 204.

The method of the present invention for analyzing a glycan structure is preferably arranged such that the specific types of product ions include product ions having m/z of 163, 204, 274, and 366, respectively.

The method of the present invention for analyzing a glycan structure is preferably arranged such that the specific types of product ions further include a product ion having m/z of 138; and in the step (b), the energy-resolved profile is created by normalizing the yield curves with use of a measured amount of the product ion having m/z of 138.

The method of the present invention for analyzing a glycan structure is preferably arranged such that in the step (a), the measuring is performed by using a sample in which a standard material which has a glycan and whose concentration is known is added in addition to the test material; the specific types of product ions further include a product ion having m/z of 138; and the method further includes the step of (e) quantifying the test material by comparing (i) a measured amount of the product ion having m/z of 138 produced from the test material and (ii) a measured amount of the product ion having m/z of 138 produced from the standard material.

The method of the present invention for analyzing a glycan structure is preferably arranged such that in the step (e), the test material is quantified on basis of (i) the measured amount of the product ion having m/z of 138 produced from the test material and (ii) the measured amount of the product ion having m/z of 138 produced from the standard material, each of which measured amounts are obtained at a value of the CID energy at which the product ion having m/z of 138 becomes maximum.

The method of the present invention for analyzing a glycan structure is preferably arranged such that the value of the CID energy at which the product ion having m/z of 138 becomes maximum is a value estimated based on a calibration curve and a value of m/z of a precursor ion of the test material to be analyzed, the calibration curve being created by (I) measuring, at various values of the CID energy, in advance the product ion having m/z of 138 in a plurality of test materials each having a glycan by MS/MS and then (II) carrying out linear regression analysis with use of (i) values of the CID energy at which measured amounts of the product ion having m/z of 138 in the plurality of test materials become maximum and (ii) values of m/z of precursor ions of the plurality of test materials.

The method of the present invention for analyzing a glycan structure is preferably arranged such that in the step (a), the measurement by MS/MS is carried out by use of a triple quadrupole mass spectrometer.

The method of the present invention for analyzing a glycan structure is preferably arranged such that the test material is a glycopeptide.

The method of the present invention for analyzing a glycan structure is preferably arranged such that the glycopeptide is a glycopeptide having an N-glycan.

The method of the present invention for analyzing a glycan structure is preferably arranged such that the glycopeptide is a glycopeptide having an O-glycan.

The embodiment of the present invention will be described below in more detail with reference to Examples below. The present invention is not limited to Examples below, but details can be changed in various manners. The present invention is not limited to the description of the embodiments above, but may be altered by a skilled person within the scope of the claims. An embodiment based on a proper combination of technical means disclosed in different embodiments is encompassed in the technical scope of the present invention. Further, all of the documents described in this specification are incorporated herein by reference

EXAMPLES

Example 1

Identification of Glycan Structure with Use of Energy-Resolved Oxonium Ion Profile FIG. 1 shows a scheme by which an energy-resolved yield curve of oxonium ions is acquired by using a triple quadrupole mass spectrometer. The following overviews this scheme. First, a glycoprotein test material (immunoglobulin in FIG. 1) is digested by trypsin into a peptide/glycopeptide mixture. The mixture thus obtained is fractionated by HPLC, and is then subjected to mass spectrometry using a triple quadrupole mass spectrometer. In the triple quadrupole mass spectrometer, a first quadrupole (Q1) isolates glycopeptide ions with unique mass (filtering), which are subsequently guided into a second quadrupole (Q2) where they undergo CID. The kinetic energy of precursor ions, which governs energy and rate of the CID in Q2, can be controlled by changing an electrode potential (corresponding to CID energy) of ion entry into Q2. A third quadrupole (Q3) filters product ions to selectively detect oligosaccharide-derived oxonium ions (see the frame A of FIG. 1) at high-sensitivity. The electrode potential of ion entry into Q2 is changed in stepwise fashion in repetitive measurements of short time intervals for each mass filter settings in Q3. In this way, energy-resolved yield curves whose horizontal axes represent an electrode potential of ion entry into Q2 and whose vertical axes represent measured ion intensity are obtained for respective types of oxonium ions (see the frame B of FIG. 1). Use of a MRM (Multiple Reaction Monitoring) mode makes it possible to simultaneously acquire energy-resolved yield curves of respective types of oxonium ions. Energy-resolved yield curves of respective types of oxonium ions obtained for a particular type of precursor ions are collectively referred to as an "energy-resolved oxonium ion profile".

Next, the following describes a specific example of how an energy-resolved oxonium ion profile is created.

The following example attempted to create energy-resolved oxonium ion profiles of various glycopeptides prepared from IgG molecule, which share the same amino acid sequence (EEQYNSTYR: SEQ ID NO: 1) but bear different glycan structures.

The glycopeptides were measured by 4000 QTRAP triple quadrupole mass spectrometer (AB Sciex, Foster City, Calif.) with Agilent 1200 nano-HPLC system (Agilent Technologies, Palo Alto, Calif.). In this example, specific types of oxonium ions (m/z=138, 163, 204, 274, and 366) were simultaneously measured by the multiple reaction monitoring mode. First, IgG tryptic digest, column-separated at a flow rate of 250 nL/min with a chip-integrated capillary column having an inside diameter of 75 μm manufactured by Nikkyo Technos, Co., Ltd. (Tokyo, Japan), was introduced to an ion source. An ion spray voltage for nanospray was set to 2200V, and a nitrogen gas was used as a curtain gas (12 psi) and a collision gas. The mass resolution of the first quadrupole (Q1) was set in a HIGH mode, the mass resolution of the third quadrupole (Q3) was set in a LOW mode, and a pause between measurements was set to 2 milliseconds. As for conditions for the CID, device parameters of CAD=4 was used, and declustering potential and entrance potential were set to 70V and 10V, respectively. The multiple reaction monitoring assay was carried out for a large number of transitions, i.e., combinations of (i) a setting value of Q1 (m/z of a target glycopeptide), (ii) a setting value of Q3 (138.05, 163, 204, 274, or 366), and (iii) a value of the CID energy which is changed by increments of 3V or 5V (since a setting value of mass at one value of the CID energy cannot be the same as that at another value of the CID energy due to software specification, the setting value of mass is, strictly speaking, changed by 0.001 as the value of the CID energy is changed, but the difference in the setting values is insignificant in the measurement). Further, the ion extraction time (Dwell Time) for each transition was set to be within a range from 20 milliseconds to 50 milliseconds so that a measurement cycle time for a single measurement target falls within around 1 second.

Energy-resolved yield curves of the respective types of oxonium ions were obtained by normalizing measured amounts of the respective types of oxonium ions with respect to the highest signal intensity (=100) of the energy-resolved yield curve of the oxonium ion of m/z=138. Although other larger-fragment oxonium ions were measured as well, plotting of such oxonium ions was omitted for simplification unless a relative amount of such oxonium ions exceeds 5%.

Figure 2:
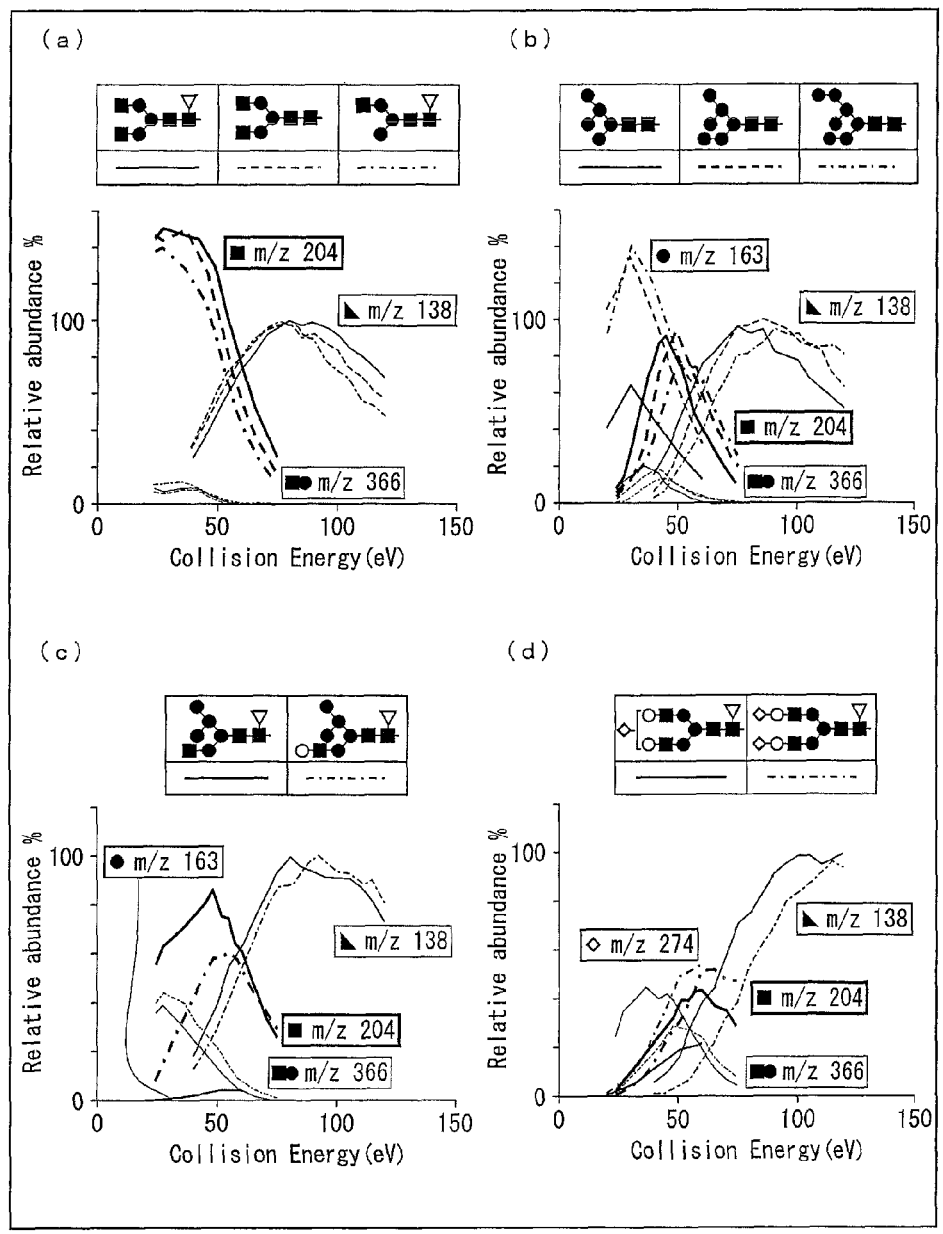
FIG. 2 is a view showing specific examples of the energy-resolved oxonium ion profile.

(a) through (d) of FIG. 2 show some examples of energy-resolved oxonium ion profiles thus created. Note that (a) through (d) of FIG. 2 each collectively show energy-resolved oxonium ion profiles of a respective plurality of glycan structures instead of showing an energy-resolved oxonium ion profile of a single glycan structure. In the schematic glycan structures shown above the energy-resolved oxonium ion profiles, the filled squares each represent N-acetylglucosamine (GlcNAc), the filled circles each represent mannose (Man), the open circles each represent galactose (Gal), the inverted triangles each represent fucose (Fuc), and the rhombuses each represent 5-acetylneuraminic acid (Neu5Ac). In (a) through (d) of FIG. 2, the energy-resolved yield curves, which correspond to the respective types of oxonium ions having respective values of m/z, are each indicated by a line whose thickness is almost same as that of a rectangular frame showing m/z of a corresponding type of oxonium ion.

(a) of FIG. 2 collectively shows energy-resolved oxonium ion profiles of three types of glycopeptides each having a non-galactosylated glycan structure. (b) of FIG. 2 collectively shows energy-resolved oxonium ion profiles of three types of glycopeptides each having a high-mannose type glycan structure. (c) of FIG. 2 collectively shows energy-resolved oxonium ion profiles of two types of glycopeptides each having a hybrid type glycan structure. (d) of FIG. 2 collectively shows energy-resolved oxonium ion profiles of two types of glycopeptides each having a sialylated glycan structure.

As shown in (a) of FIG. 2, measured amounts of the oxonium ion of m/z=204 (GlcNAc) in the glycopeptides each having a non-galactosylated glycan structure were apparently greater than those of the oxonium ion of m/z=204 in other glycopeptides having the same number of GlcNAc (see, for example, (c) or (d) of FIG. 2). It is hypothesized that this is because the precursor ions are protonated so that GlcNAc becomes a leaving group.

As shown in (b) of FIG. 2, measured amounts of the oxonium ion of m/z=163 (hexose) in the glycopeptides each having the high-mannose type glycan structure were apparently greater than those in other glycopeptides. Since almost no oxonium ion of m/z=163 was measured in the glycopeptides each having the hybrid type glycan structure ((c) of FIG. 2), the high yield of the oxonium ion of m/z=163 in the glycopeptides each having the high-mannose type glycan structure cannot be explained by the number of mannosyl linkages alone. A possible explanation for such a difference is that mannose or galactose which is in proximity to GlcNAc lacks a labile proton needed for oxonium ion formation.

As shown in (a) through (d) of FIG. 2, the glycopeptides exhibited energy-resolved oxonium ion profiles that can be distinguished from one another although a characteristic pattern could be observed for each type of glycan structure (non-galactosylated type, high-mannose type, hybrid type, or sialylated type).

Figure 3:
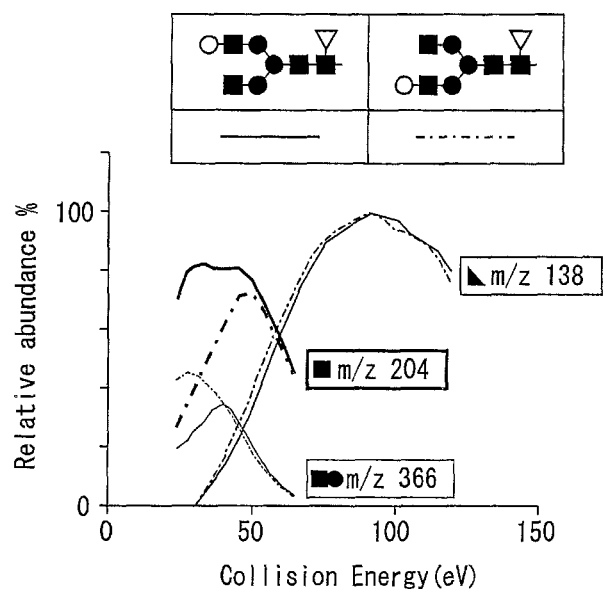
FIG. 3 is a view showing other specific examples of the energy-resolved oxonium ion profile.

This analysis revealed that even glycopeptide isoforms each of which has a glycan structure of 4[Hex]4[GlcNAc]1[Fuc] and which are different only in linkage position of terminal galactose (one of them has terminal galactose at a α1-3 branch, whereas the other one of them has terminal galactose at a α1-6 branch can be distinguished from each other (FIG. 3). As shown in FIG. 3, these isoforms were different at least in energy-resolved yield curve of the oxonium ion of m/z=366. That is, the isoform having terminal galactose at the α1-6 branch was higher in yield of the oxonium ion of m/z=366 at low electrode potentials than the isoform having terminal galactose at the α1-3 branch. In a case where a mixture test material of these isomers (mixed at a ratio of 1:1 or 1:2) was measured, a yield curve of the oxonium ion of m/z=366 was constructed between the yield curves of the oxonium ion of m/z=366 that are obtained by analyzing these isomers separately. This shows that use of the present analysis method utilizing an energy-resolved oxonium ion profile makes it possible to predict an abundance ratio of structural isomers in a mixture test material without the need to separate the isomers by chromatography. Note that the same explanation as that for the schematic glycan structures shown in FIG. 2 can be applied to the schematic glycan structures shown in FIG. 3.

Example 2

Prediction Using Linear Regression Analysis

In Example 2, model data was obtained by subjecting test materials whose glycan structures are known to similar measurement and data processing to those in Example 1 and then linear regression analysis using this model data was carried out.

Figure 11:
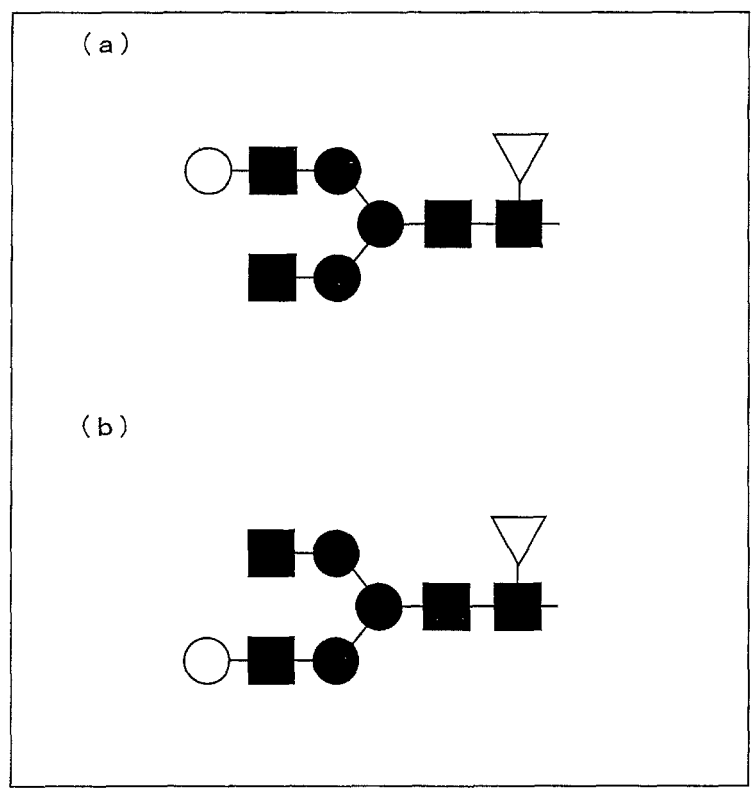
FIG. 11 is a view showing glycan structures used for prediction of identity of patterns by linear regression analysis.

First, two types of glycopeptides having the glycan structures shown in (a) and (b) of FIG. 11, respectively, were prepared, and measured values of respective types of product ions at each value of CID energy were obtained. These glycopeptides are identical in mass but are different from each other in structure. For convenience, the glycan structure shown in (a) of FIG. 11 was set to 0 and the glycan structure shown in (b) of FIG. 11 was set to 1. These values 0 and 1 were used as an objective variable Y for specifying a type of a glycan structure. Note that the same explanation as that for the schematic glycan structures shown in FIG. 2 can be applied to the schematic glycan structures shown in FIG. 11. Normalized intensities (measured values) of the respective types of product ions measured at each value of CID energy were used as a dependent variable X. Specifically, the linear regression analysis was carried out by measuring each of the glycan structures ten times while using, as the dependent variable, a total of 24 measured values, i.e., (i) measured values of a product ion of m/z=204 at 12 points of CID energy (24, 27, 30, 33, 36, 39, 42, 45, 50, 55, 60, and 65 eV) and (ii) measured values of a product ion of m/z=366 at 12 points of CID energy (24, 27, 30, 33, 36, 39, 42, 45, 50, 55, 60, and 65 eV).

As a result, the following estimation equation was obtained:

$$Y = -1.64X_1 + 0.817X_2 + 0.345X_3 + 0.284X_4 + 7.138X_5 + 0.297X_6 - 0.384$$

where $X_1$ through $X_6$ represent a measured value of the product ion of m/z=366 at CID energy of 24 eV, a measured value of the product ion of m/z=204 at CID energy of 27 eV, a measured value of the product ion of m/z=204 at CID energy of 36 eV, a measured value of the product ion of m/z=204 at CID energy of 42 eV, a measured value of the product ion of m/z=366 at CID energy of 65 eV, and a measured value of the product ion of m/z=204 at CID energy of 39 eV, respectively. If the data of the glycan structure shown in (a) of FIG. 11 is assigned to the estimation equation, Y becomes a value close to 0, whereas if data of the glycan structure shown in (b) of FIG. 11 is assigned to the estimation equation, Y becomes a value close to 1. Obtained values of Y which fall within a confidence interval of 95% of this model can be determined as significant judgment results.

Other plural types (three types) of test materials each having an identical glycan structure to that shown in (b) of FIG. 11 were each measured twice, and a value of Y was obtained for each of these types of test materials. As a result, two types of test materials each exhibited an estimated value of Y which was close to 1 and was within the 95% confidence interval. Therefore, these two types of test materials can be judged to have the glycan structure shown in (b) of FIG. 11.

Next, data of a test material having a glycan structure different from both of the glycan structure shown in (a) of FIG. 11 and the glycan structure shown in (b) of FIG. 11 was obtained and assigned to the estimation equation. As a result, this test material exhibited an estimated value of approximately 2. This result showed that this test material had a structure different from the glycan structure shown in (a) of FIG. 11 and the glycan structure shown in (b) of FIG. 11.

Example 3

High-Sensitivity Quantification of Glycopeptides

An observation of various energy-resolved oxonium ion profiles revealed that energy-resolved yield curve shapes of the oxonium ion of m/z=138 were similar among tested glycan structures. To clarify this, the following test was conducted.

(Materials)

As human immunoglobulin (IgG) test materials, Cetuximab was purchased Merck Serono (Tokyo, Japan) and Trastuzumab was purchased from Chugai Seiyaku (Osaka, Japan). These test materials were digested by trypsin. As a result, standard materials containing a large variety of glycopeptides were obtained. Specifically, 80 μg of each of these test materials was dissolved in 33 μl of 8 M urea solution. To the solution thus obtained, 1.7 μL of a dithiothreitol-triethylammonium bicarbonate solution (100 mM dithiothreitol, 1 M triethylammonium bicarbonate) was added. The mixture was reduced at 55° C. for 30 minutes. Next, after addition of 3.5 μL of 0.5M iodoacetate, the mixture was alkylated at room temperature in a dark place for 30 minutes, and was then diluted with 300 μL of a dithiothreitol-triethylammonium bicarbonate solution (2.5 mM dithiothreitol, 25 mM triethylammonium bicarbonate). Thereto, 4 μg of lysyl endopeptidase (Wako Pure Chemical Industries, Ltd.) was added, and after 2 hours of reaction at 37° C., 4 μg of Trypsin Gold (Promega KK) was added. After 4 hours of digestion reaction, the mixture was diluted with 700 μL of a 3% acetonitrile solution, and was then subjected to desalting purification with the use of an OASIS HLB solid-phase extraction cartridge (Nihon Waters K.K.). Here, a flow-through fraction and a 15% acetonitrile elusion fraction were separately collected. The flow-through fraction and the elusion fraction were diluted with a 0.1% acetic acid solution twofold and fivefold, respectively. These fractions were used as standard measurement materials. The flow-through fraction contained a glycopeptide group having the amino acid sequence EEQYNSTYR (SEQ ID NO: 1), and the 15% acetonitrile elusion fraction contained a glycopeptide group having the amino acid sequence MNSLQSNDTAIYYCAR (SEQ ID NO: 2) (only Cetuximab).

(Device Settings and Measurement Method)

The measurement test materials were measured by the MRM mode of 4000 QTRAP triple quadrupole mass spectrometer (AB Sciex, Foster City, Calif.) with nano-HPLC system. Conditions for the measurement were similar to those in Example 1. Note, however, that the multiple reaction monitoring assay was carried out for a large number of transitions, i.e., combinations of (i) a setting value of Q1 (m/z of a target glycopeptide), (ii) a setting value of Q3 (fixed to 138.05), and (iii) a value of the CID energy which is changed by increments of 3V or 5V (since a setting value of mass at one value of the CID energy cannot be the same as that at another value of the CID energy due to software specification, the setting value of mass is, strictly speaking, changed by 0.001 as the value of the CID energy is changed, but the difference in the setting values is insignificant in the measurement).

(Data Processing Method)

Measured data was loaded with analysis software MultiQuant ver.2.02, and was subjected, for each transition, to peak integration of mass chromatogram under a condition of a smoothing width of 1 point. The integrated values were exported to spreadsheet software, and a table in which CID energy setting values and the integrated values are associated with one another was created. In this table, integrated values for each transition were normalized as percentage relative to the maximum integrated value in the data set. Each glycopeptide was measured three times, and an average of normalized integrated values was obtained. Based on the data thus obtained, CID energy (optimum CID energy) at which generation efficiency of the product ion of m/z=138 became maximum was obtained for each glycopeptide. The optimum CID energy was defined as a CID energy setting value of a transition in which the average peak integrated value is closest to 100. Note, however, that in a case where the same integrated value falling in a range from 98 to 100 was successively obtained, an average of CID energy values associated with these integrated values was used as the optimum CID energy. The result is shown in Table 1.

TABLE 1

| Sample NO | Amino acid sequence | Constituents of N-glycan | | | | m/z | Optimum CID energy |
| --- | --- | --- | --- | --- | --- | --- | --- |
| | | The number of HexNAc | The number of Hex | The number of Fuc | The number of SA | | |
| 1 | EEQYNSTYR | 3 | 3 | 1 | 0 | 811.4 | 75 |
| 2 | EEQYNSTYR | 3 | 4 | 0 | 0 | 816.7 | 75 |
| 3 | EEQYNSTYR | 3 | 4 | 1 | 0 | 865.4 | 80 |
| 4 | EEQYNSTYR | 3 | 4 | 0 | 1 | 913.8 | 95 |
| 5 | EEQYNSTYR | 3 | 5 | 1 | 0 | 919.4 | 90 |
| 6 | EEQYNSTYR | 4 | 3 | 0 | 0 | 830.3 | 80 |
| 7 | EEQYNSTYR | 4 | 3 | 1 | 0 | 878.1 | 82.5 |
| 8 | EEQYNSTYR | 4 | 4 | 0 | 0 | 884.4 | 85 |
| 9 | EEQYNSTYR | 4 | 4 | 0 | 1 | 981.4 | 90 |
| 10 | EEQYNSTYR | 4 | 4 | 1 | 0 | 933.1 | 90 |
| 11 | EEQYNSTYR | 4 | 4 | 1 | 1 | 1030.1 | 105 |
| 12 | EEQYNSTYR | 4 | 5 | 0 | 0 | 938.4 | 95 |
| 13 | EEQYNSTYR | 4 | 5 | 1 | 0 | 987.1 | 95 |
| 14 | EEQYNSTYR | 4 | 5 | 0 | 1 | 1035.5 | 105 |
| 15 | EEQYNSTYR | 4 | 5 | 1 | 1 | 1084.2 | 100 |
| 16 | EEQYNSTYR | 5 | 3 | 0 | 0 | 898.1 | 90 |
| 17 | EEQYNSTYR | 5 | 3 | 1 | 0 | 952.1 | 100 |
| 18 | EEQYNSTYR | 5 | 4 | 0 | 0 | 946.8 | 90 |
| 19 | EEQYNSTYR | 5 | 4 | 1 | 0 | 1000.8 | 92.5 |
| 20 | MNSLQSNDTAIYYCAR | 5 | 8 | 1 | 0 | 1092.5 | 109 |
| 21 | MNSLQSNDTAIYYCAR | 5 | 9 | 1 | 0 | 1133.1 | 110 |
| 22 | MNSLQSNDTAIYYCAR | 4 | 7 | 1 | 0 | 1001.3 | 95 |
| 23 | MNSLQSNDTAIYYCAR | 4 | 6 | 2 | 0 | 997.3 | 100 |

TABLE 1-continued

| | | Constituents of N-glycan | | | | | |
|---|---|---|---|---|---|---|---|
| Sample NO | Amino acid sequence | The number of HexNAc | The number of Hex | The number of Fuc | The number of SA | m/z | Optimum CID energy |
| 24 | MNSLQSNDTAIYYCAR | 4 | 6 | 1 | 0 | 960.7 | 91 |
| 25 | MNSLQSNDTAIYYCAR | 4 | 5 | 1 | 1 | 997.1 | 100 |
| 26 | MNSLQSNDTAIYYCAR | 4 | 4 | 1 | 0 | 879.7 | 86 |
| 27 | MNSLQSNDTAIYYCAR | 4 | 5 | 1 | 0 | 920.2 | 97 |
| 28 | MNSLQSNDTAIYYCAR | 4 | 3 | 1 | 0 | 839.2 | 80 |

Figure 4:
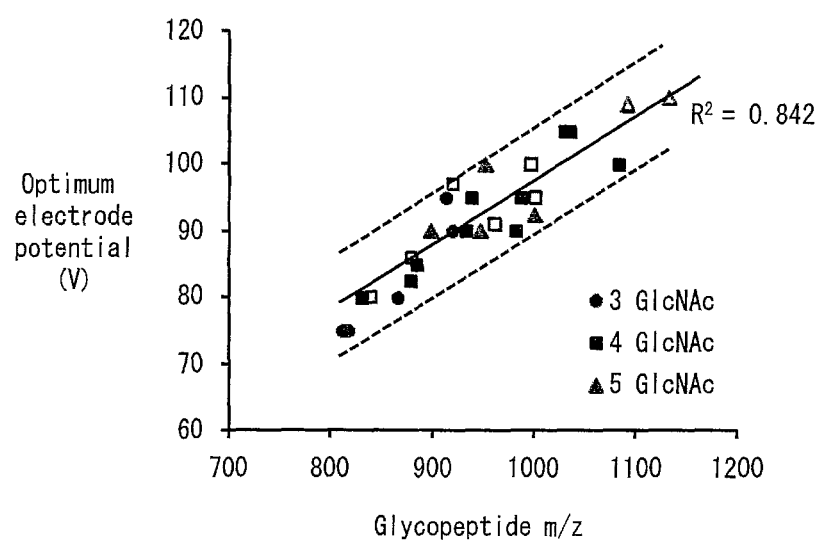
FIG. 4 is a scatter diagram showing a correlation between an optimum CID energy value and an m/z value of precursor ions.

HexNAc: N-acetylhexosamine,
Hex: hexose (6-carbon sugar),
Fuc: fucose,
SA: sialic acid Based on the result shown in Table 1, a scatter diagram was created by plotting m/z of glycopeptides in an X-axis direction and optimum CID energy values in a Y-axis direction (FIG. 4). In FIG. 4, the circles each represent data of a glycopeptide containing three GlcNAc, the squares each represent data of a glycopeptide containing four GlcNAc, and the triangles each represent data of a glycopeptide containing five GlcNAc. Out of these marks, the open ones each represent data of a glycopeptide whose peptide linked with a glycan has the amino acid sequence MNSLQSNDTAIYYCAR (SEQ ID NO: 2), and the filled ones each represent data of a glycopeptide whose peptide linked with a glycan has the amino acid sequence EEQYNSTYR (SEQ ID NO: 1). As shown in FIG. 4, this scatter diagram suggested a linear correlation between m/z of the glycopeptides and the optimum CID energy values. As a result of collinear approximation by linear regression, there observed an extremely strong correlation having a multiple correlation coefficient ($R^2$) of 0.842. All the points, which are plotted on the scatter diagram so as to be distinguished from one another according to differences in the number of GlcNAc and in amino acid sequence, are located in the vicinity of an approximate curve. This shows that factors such as the differences in the number of HexNAc and in amino acid sequence do not influence the correlation. The fact that a glycan structure, an amino acid sequence of a peptide, and the charge number do not influence a correlation between m/z of glycopeptides and the optimum CID energy values means that an estimated value of optimum CID energy for any type of test material can be calculated on the basis of this approximate curve.

Figure 5:
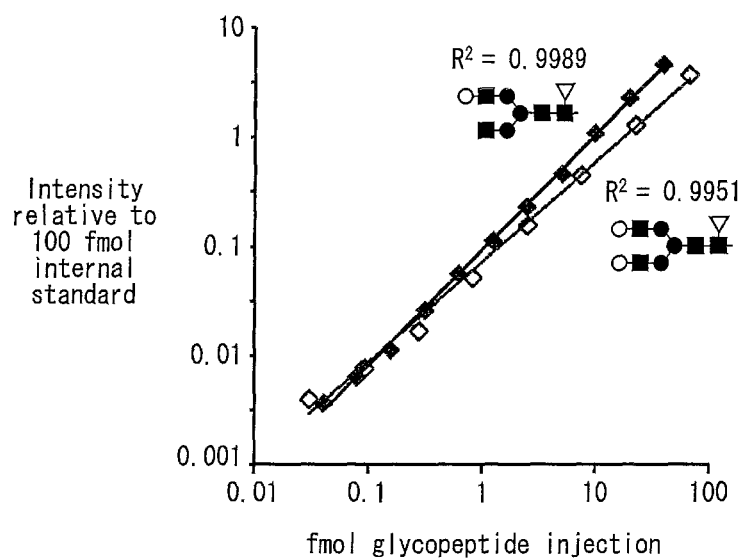
FIG. 5 is a view showing a correlation between injection concentration of a test material to be measured and concentration of an internal standard.

Next, the oxonium ion of m/z=138 in glycopeptides was measured at the optimum CID energy by multiple reaction monitoring mode while using a glycopeptide whose mass is known as a standard, and detection sensitivity of the glycopeptides was examined. As a result, the detection sensitivity of 30 attomol (injection amount) was observed in two types of isolated glycopeptides and there observed linearity of signal intensities in a wide range from 30 attomol to 30 femtomol (FIG. 5). This result shows that the method of the present invention in which the oxonium ion of m/z=138 is measured at the optimum CID energy achieves measurement sensitivity and quantitative performance exceeding those of a conventional method for glycopeptide measurement. Note that the value of $R^2$ in FIG. 5 indicates a multiple correlation coefficient. Note also that the same explanation as that for the schematic glycan structures shown in FIG. 2 can be applied to the schematic glycan structures shown in FIG. 5.

Example 4

Dual Monitoring of Glycoform in Fc and Fab Regions of Antibody

Figure 6:
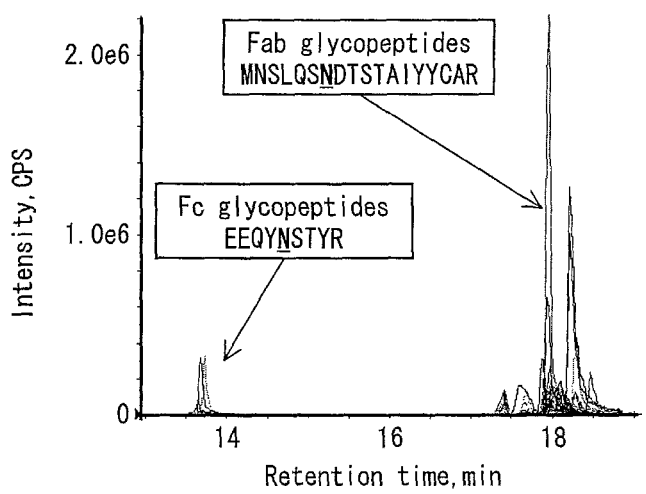
FIG. 6 is a view showing an MRM chromatogram monitoring oxonium ions of m/z=138 in digested cetuximab.

Site-specific glycan structure analysis of a glycoprotein was attempted which analysis combines oxonium ion (m/z=138) monitoring and energy-resolved oxonium ion profiling for quantification and verification of each structure, respectively. As a test material to be analyzed, cetuximab (Merck Serono Co., Ltd.) which is a therapeutic antibody was used. The test material was denatured and digested in a similar manner to Example 2. With the use of the OASIS HLB solid-phase extraction cartridge, an undigested protein was removed from the test material thus digested and then the test material was desalted and purified. The peptide eluate was diluted and subjected to mass spectrometry using a triple quadrupole mass spectrometer with nano-HPLC. In the triple quadrupole mass spectrometer, the oxonium ion (m/z=138) was measured for all currently predicted 40 types of glycoforms by the MRM mode (FIG. 6). In the chromatogram of FIG. 6, the horizontal axis represents a retention time in LC, and the vertical axis represents the intensity of the oxonium ion (m/z=138) which is expressed by the count number of the oxonium ion.

As shown in FIG. 6, a peak was observed within a range of retention time of 13 to 14 minutes and within a range of retention time of 17 to 19 minutes. The peak within the range of retention time of 13 to 14 minutes corresponds to a glycopeptide (amino acid sequence: EEQYN$_{297}$STYR, SEQ ID NO: 1) in the Fc region, and the peak within the range of retention time of 17 to 19 minutes corresponds to a Fab glycopeptide (amino acid sequence: MNSLQSN$_{88}$DTAIYYCAR SEQ ID NO: 2). It is thus possible to simultaneously analyze, by a single analysis, two types of glycopeptides that are different from each other in glycosylation site.

Figure 7:
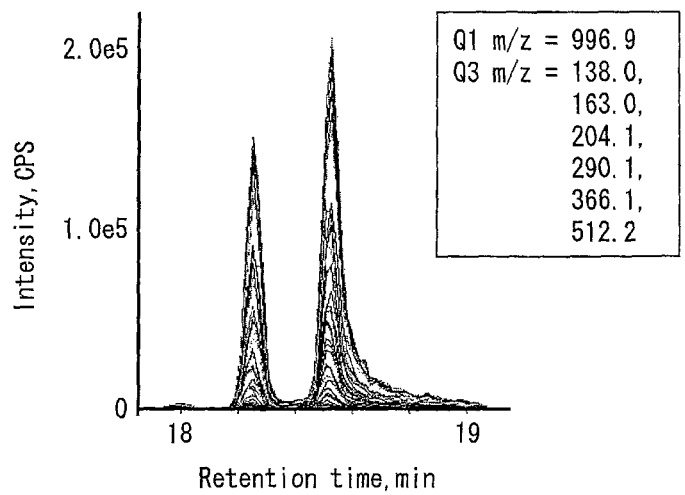
FIG. 7 is a view showing an MRM chromatogram obtained from a glycan containing galactose-1,3-galactose or N-glycolylneuraminic acid motif in digested cetuximab.

Although the retention time in reversed-phase HPLC is mainly determined by an amino acid composition, there observed, in the present analysis method, a wide range of retention time arising solely from glycoform difference, including baseline separation of glycopeptides which have almost identical molecular weight. For example, Neu5Gc has molecular weight 307 Da and is smaller only by 1 Da than combined mass of hexose and fucose (308 Da). Therefore glycopeptides whose predicted structure contain Neu5Gc often result in two peaks on MRM chromatogram (FIG. 7)

due to crosstalk with similar glycopeptide with Neu5Gc substituted with hexose and fucose.

The present analysis led to discovery of hyperfucosylated glycan structures. Further, it was found out that hyperfucosylated form was absent for hypergalactosylated or disialylated structures, and it was therefore speculated that extra fucosylation occurs on antennary GlcNAc (a branch at a non-reducing terminal of a core structure), which forms a Lewisxmotif, in a competitive manner with terminal galactosylation (α-Gal) or sialylation (Neu5Gc) for unmodified antenna.

To demonstrate this, structures of antennas in a biantennary structure, which has two antennas, and a triantennary structure, which has three antennas, were analyzed by quantification using oxonium ion (m/z=138) monitoring and by structure verification using an energy-resolved oxonium ion profile. The result is shown in Table 2.

TABLE 2

| Composition | | | % Abundance | |
| --- | --- | --- | --- | --- |
| α-Gal | Lewis X | Neu5Gc | Biantennary | Triantennary |
| 1 | — | — | 6.4 | 1.1 |
| — | 1 | — | 0.7 | 0.2 |
| — | — | 1 | 7.1 | 0.9 |
| 2 | — | — | 25.9 | 1.7 |
| 1 | 1 | — | 2.5 | 1.0 |
| 1 | — | 1 | 18.5 | 1.3 |
| — | 2 | — | 0.2 | 0.1 |
| — | 1 | 1 | 1.0 | 0.2 |
| — | — | 2 | 3.3 | 0.3 |
| 3 | — | — | — | 2.5 |
| 2 | 1 | — | — | 1.0 |
| 2 | — | 1 | — | 1.8 |
| 1 | 2 | — | — | 0.2 |
| 1 | 1 | 1 | — | 0.5 |
| 1 | — | 2 | — | 0.6 |
| — | 3 | — | — | 0.0 |
| — | 2 | 1 | — | 0.1 |
| — | 1 | 2 | — | 0.2 |
| — | — | 3 | — | N.D. |

(Antenna occupancy = 1 for the first three rows; Antenna occupancy = 2 for the next six rows; Antenna occupancy = 3 for the remaining rows.)

N.D. = Not Detected

In Table 2, the "α-Gal" column shows the number of galactosylated antennas, the "Lewis X" column shows the number of antennas with Lewisxmotif, and the "Nue5Gc" column shows the number of sialylated antennas. The "biantennary" column shows percentages of those of examined biantennary structures which had the glycan structure(s) shown on the left side in a corresponding row, and the "triantennary" column shows percentages of those of examined triantennary structures which had the glycan structure(s) shown on the left side in a corresponding row. For example, out of the examined biantennary structures, percentage of biantennary structures whose one antenna was galactosylated and other antenna was sialylated was 18.5%.

As a result, in the biantennary structures in which only one antenna was modified, galactosylation, sialylation, and formation of a Lewisxmotif occurred at a ratio of 46:50:5. This is estimated to reflect the relative catalytic rates of glycosyltransferases. However, in the bianntennary structures in which both of the antennas were modified, relative abundances of a second antenna exhibited a different pattern from a first antenna, tending strongly to galactosylation. This suggests that modification of the first antenna affected the reactivity of the second antenna.

Figure 8:
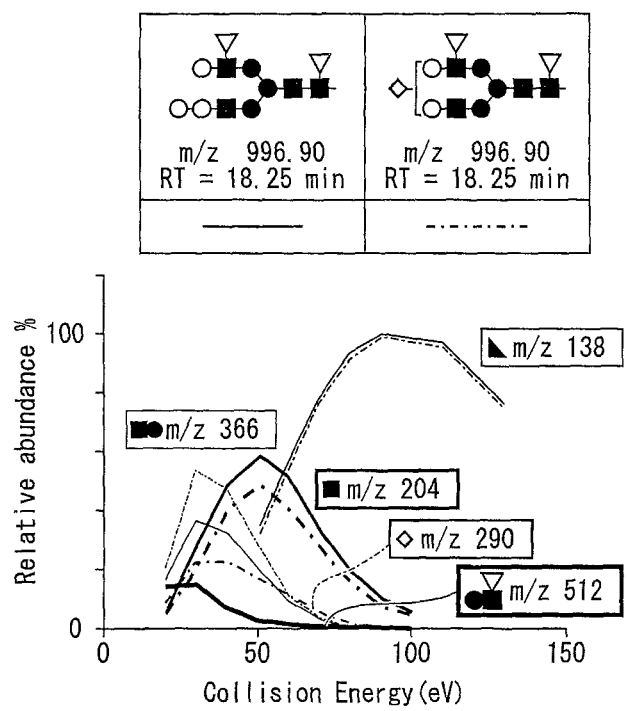
FIG. 8 is a view showing energy-resolved oxonium ion profiles of two types of glycopeptide containing Lewisxmotif.

FIG. 8 shows energy-resolved oxonium ion profiles of two types glycopeptides containing Lewisxmotif. In the energy-resolved oxonium ion profiles, an oxonium ion of m/z=290 and an oxonium ion of m/z=512 were also detected and plotted. The same explanation as that for the schematic glycan structures shown in FIG. 2 can be applied to the schematic glycan structures shown in FIG. 8. FIG. 8 shows that structures predicted to contain Lewisxmotif were signified by high-level detection of the oxonium ion of m/z=512 which corresponds to [Hex+GlcNAc+Fuc]oxonium ion.

Other features of cetuximab revealed in this analysis were in accordance with previous reports. For example, the most major glycoform in Fc glycan was an non-galactosylated biantennary structure, and relatively high level of hybrid and high-mannose structures were also detected.

It was thus demonstrated that the present analysis method was capable of monitoring glycan heterogeneity of both Fc and Fab regions with high accuracy and high sensitivity.

Example 5

Lot-to-lot Heterogeneity of Glycoform of Therapeutic Antibody

Example 5 evaluated the analysis method of the above embodiment for applicability to lot-to-lot quality control analysis of glycan heterogeneity, by using four non-continuous lots of trastuzumab (Chugai Pharmaceutical Co., Ltd.) and four non-continuous lots of bevacizumab (Chugai Pharmaceutical Co., Ltd.).

Figure 9:
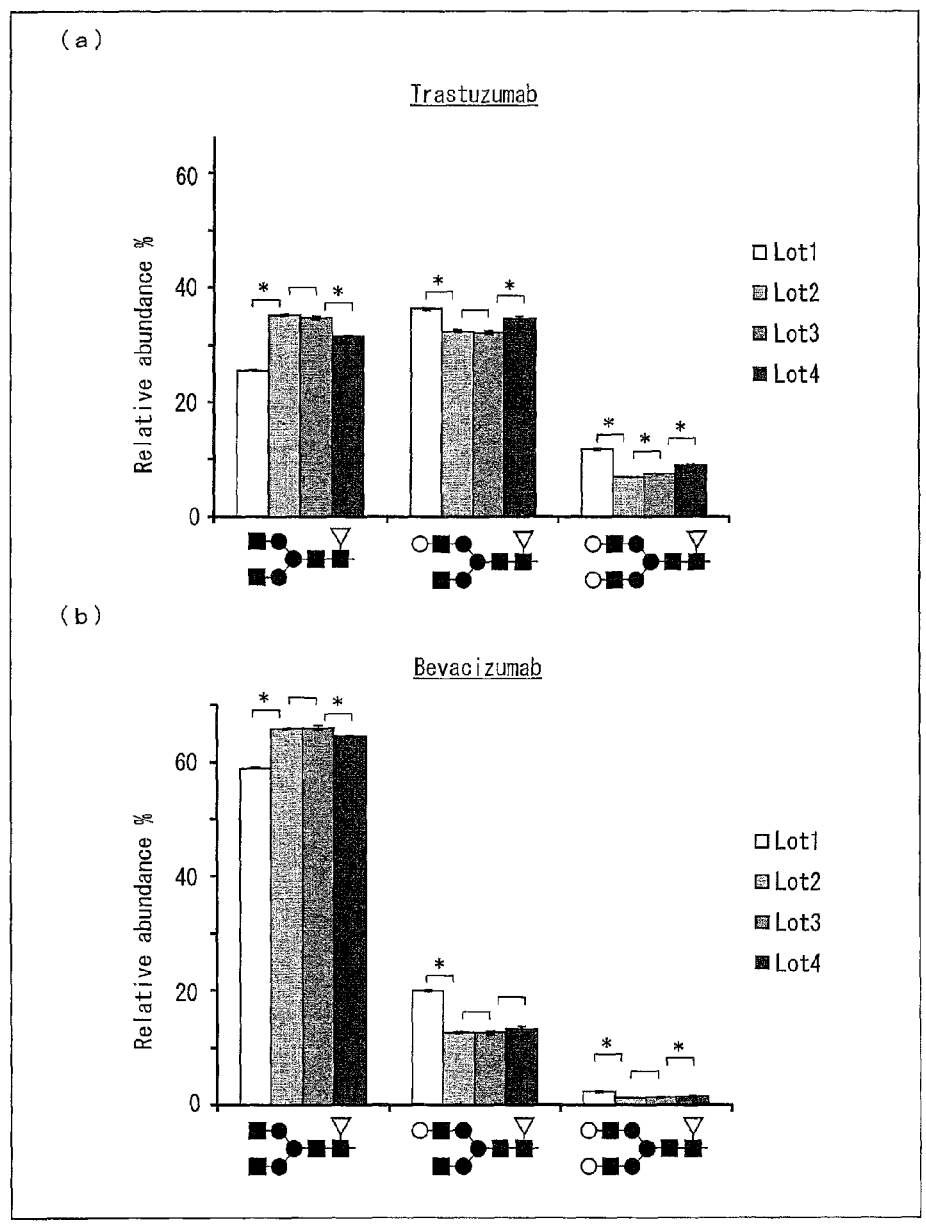
FIG. 9 is a view showing a result of analysis on lot-to-lot heterogeneity of glycoform of a therapeutic antibody.

The test materials were denatured, digested, and purified in a similar manner to cetuximab in Example 2, and were then subjected to mass spectrometry using a triple quadrupole mass spectrometer with a nano-HPLC, so as to verify and quantify glycan structures. In the mass spectrometry, glycopeptides having the amino acid sequence represented by SEQ ID NO: 1 were measured. The lots were numbered in a production order. Analysis was performed three times for each lot, and statistical significance of a difference between two consecutive lots was evaluated by Student's t-test. The result is shown in FIG. 9. (a) of FIG. 9 shows a result concerning trastuzumab, and (b) of FIG. 9 shows a result concerning bevacizumab. In both of (a) and (b) of FIG. 9, abundance ratios of three types of glycan structures are shown. The same explanation as that for the schematic glycan structures shown in FIG. 2 can be applied to the schematic glycan structures shown in FIG. 9.

As shown in FIG. 9, there observed a significant difference in abundance ratios of the glycan structures between Lot1 and Lot2. Meanwhile, in both of the antibodies, there observed almost no difference between Lot2 and Lot3. However, there observed again a significant difference between Lot3 and Lot4. In FIG. 9, the "**" marks each indicate $p<0.05$ in the Student's t-test. A glycoform that was most prone to lot-to-lot variability was the frequency of galactosylation onto GlcNAc in a biantennary structure. This means that either an enzyme expression level or a rate of antibody production can change by environmental factors. A decrease in abundance of galactosylated form was clearly compensated by an increase in abundance of non-galactosylated form. Moreover, as a result of observation, bevacizumab contained a non-glycosylated peptide (peptide consisting of the amino acid sequence represented by SEQ ID NO: 1) and that an amount of this peptide is also prone to variation. Because glycopeptide detection by oxonium ion (m/z=138) monitoring was about 10-fold more sensitive than detection of a non-glycosylated counterpart, actual percentage of non-glycosylated counterpart peptide could be as high as a few percent and deserves good attention for quality control.

Example 6

Analysis of Glycopeptide Having O-Glycan

In Example 6, a Human Transferrin-derived glycopeptide having an O-glycan was analyzed.

Similar processes to those for human immunoglobulin (IgG) in Example 1 were carried out up to the tryptic digestion. After the tryptic digestion, a mixture thus prepared was heated at 100° C. for 10 minutes so as to inactivate trypsin. Thereto, proline specific endopeptidase (Toyobo Co., Ltd.) whose amount is 1/20 (w/w) of Human Transferrin used for the digestion was added. After reaction at 37° C. for 8 hours, acetonitrile which is three times in volume (v/v) was added so as to obtain 75% acetonitril solution. This solution was desalted by hydrophillic solid-phase extraction plate HILIC μElution (Nihon Waters K.K.). In this desalting process, 100 mM of a triethylammonium bicarbonate 75% acetonitrile solution was used as a solid phase equilibrium and washing buffer, and 100 mM of a triethylammonium bicarbonate 25% acetonitrile solution was used as an extraction buffer from a solid phase. An eluate thus obtained was dried to solid by Speedvac, and was then redissolved in ultrapure water. A solution thus obtained was used as a measurement test material to be subjected to mass spectrometry. Measurement and data processing of oxonium ions were carried out for a plurality of transitions in which m/z of precursor ions was set to 991.4 and only the CID energy was changed as in Example 1. The glycopeptide which is the measurement test material is summarized as follows: amino acid sequence: $S_{52}$DGPSVACVK (SEQ ID NO: 3, Ser52 is a glycosylation site), glycan composition: HexNAc×3, Hex×2, Fuc×1, Neu5AC×3 (composition which an N-glycan nerver has), peptide mass (MW): 1018.5, glycan mass (MW): 1970.7, glycopeptide mass (MW): 2971.2 (−18Da because of O-glycan linkage), measurement ion: m/z=991.4(3+).

Figure 10:
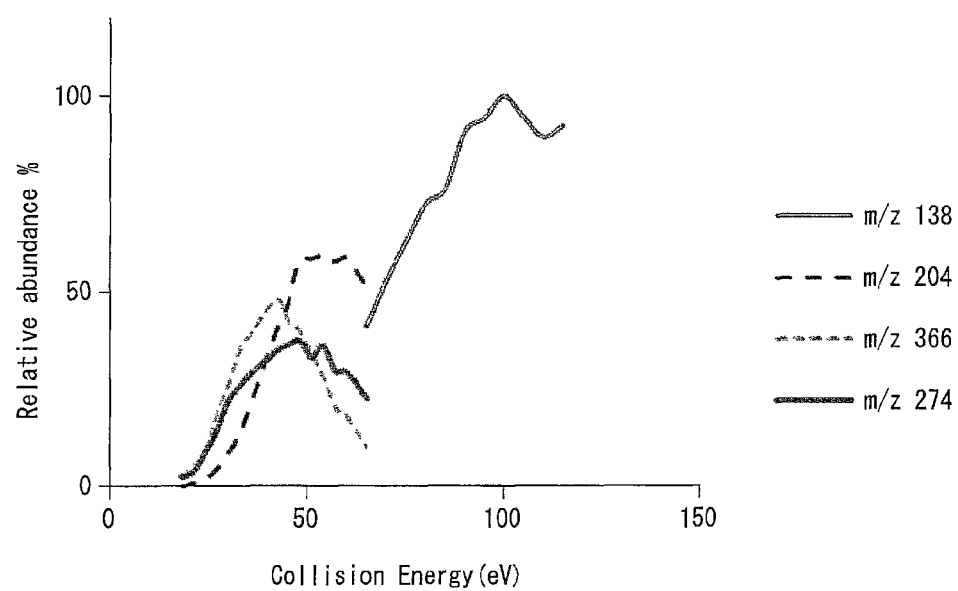
FIG. 10 is a view showing an energy-resolved oxonium ion profile of an O-glycopeptide.

As a result, the energy-resolved oxonium ion profile shown in FIG. 10 was obtained. The energy-resolved oxonium ion profile shown in FIG. 10 is utterly different from that obtained from an N-glycopeptide having sialic acid. It is thus possible to obtain higher-level information of even a glycan structure of an O-glycopeptide that is greatly different from an N-glycopeptide in form of a glycan structure. Further, it was confirmed that, also in an O-glycopeptide, generation efficiency of m/z becomes maximum at optimum CID energy estimated from m/z of the glycopeptide of Example 6 with the use of the linear correlation (Example 2) between m/z of glycopeptides and the optimum CID energy value.

INDUSTRIAL APPLICABILITY

The present invention is applicable to analysis of a glycan structure of a glycoprotein, and is, for example, suitably applicable in quality control tests of glycan structures of biotechnology-based drugs such as therapeutic antibodies.

---

The invention claimed is:

1. A method for analyzing a glycan structure with use of a mass spectrometer that carries out MS/MS measurement, comprising the steps of:
   (A) carrying out MS/MS measurement at various values of CID energy, the step (A) including the step (a) of causing a first quadrupole mass filter to isolate glycopeptide ions from test materials having a glycan and the step (b) of causing a second quadrupole mass filter to filter specific types of product ions derived from the glycopeptide ions and detecting amounts of the specific types of product ions at the values of CID energy;
   (B) creating energy-resolved profiles including yield curves representing relationships between (i) the values of the CID energy and (ii) measured amounts of the respective specific types of product ions; and
   (C) distinguishing the glycan structure by comparing the energy-resolved profiles of the respective test materials obtained in the step (B),
   the specific types of product ions being derived from a protonated monosaccharide or disaccharide.

2. The method according to claim 1, wherein the step (C) is the step of determining which of glycan structure isoforms the glycan structure is.

3. The method according to claim 1, wherein the step (b) is the step of causing the second quadrupole mass filter to filter specific types of product ions whose m/z is 100 to 500 and detecting amounts of the specific types of product ions.

4. The method according to claim 3, wherein the step (b) is the step of causing the second quadrupole mass filter to filter specific types of product ions whose m/z is 1.00 to 300 and detecting amounts of the specific types of product ions.

5. A method for analyzing a glycan structure with use of a mass spectrometer that carries out MS/MS measurement, comprising the steps of:
   (A) carrying out MS/MS measurement at various values of CID energy, the step (A) including the step (a) of causing a first quadrupole mass filter to isolate glycopeptide ions from test materials baying a glycan and the step (b) of causing a second quadrupole mass filter to filter specific types of product ions derived from the glycopeptide ions and detecting amounts of the specific types of product ions at the various values of CID energy; and
   (B) distinguishing the glycan structure by linear regression analysis using (i) the values of the CID energy and (ii) measured amounts of the respective specific types of product ions,
   the specific types of product ions being derived from a protonated monosaccharide or disaccharide.

6. The method according to claim 5, wherein the step (B) is the step of determining which of glycan structure isoforms the glycan structure is.

7. The method according to claim 5, wherein the step (b) is the step of causing the second quadrupole mass filter to filter specific types of product ions whose m/z is 100 to 500 and detecting amounts of the specific types of product ions.

8. The method according to claim 7, wherein the step (b) is the step of causing the second quadrupole mass filter to filter specific types of product ions whose m/z is 100 to 300 and detecting amounts of the specific types of product ions.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Homo sapiens
<220> FEATURE:
<221> NAME/KEY: CARBOHYD
<222> LOCATION: (5)..(5)

<400> SEQUENCE: 1

Glu Glu Gln Tyr Asn Ser Thr Tyr Arg
1               5

<210> SEQ ID NO 2
<211> LENGTH: 16
<212> TYPE: PRT
<213> ORGANISM: Homo sapiens
<220> FEATURE:
<221> NAME/KEY: CARBOHYD
<222> LOCATION: (7)..(7)

<400> SEQUENCE: 2

Met Asn Ser Leu Gln Ser Asn Asp Thr Ala Ile Tyr Tyr Cys Ala Arg
1               5                   10                  15

<210> SEQ ID NO 3
<211> LENGTH: 10
<212> TYPE: PRT
<213> ORGANISM: Homo sapiens
<220> FEATURE:
<221> NAME/KEY: CARBOHYD
<222> LOCATION: (1)..(1)

<400> SEQUENCE: 3

Ser Asp Gly Pro Ser Val Ala Cys Val Lys
1               5                   10
```